(12) United States Patent
Imagawa

(10) Patent No.: US 10,041,039 B2
(45) Date of Patent: Aug. 7, 2018

(54) METHOD FOR PRODUCING PLURIPOTENT STEM CELLS DERIVED FROM DENTAL PULP

(71) Applicant: JCR Pharmaceuticals Co., Ltd., Hyogo (JP)

(72) Inventor: Kiwamu Imagawa, Hyogo (JP)

(73) Assignee: JCR PHARMACEUTICALS CO., LTD., Hyogo (JP)

( * ) Notice: Subject to any disclaimer, the term of this patent is extended or adjusted under 35 U.S.C. 154(b) by 672 days.

(21) Appl. No.: 14/388,464

(22) PCT Filed: Mar. 28, 2013

(86) PCT No.: PCT/JP2013/059201
§ 371 (c)(1),
(2) Date: Oct. 30, 2014

(87) PCT Pub. No.: WO2013/146992
PCT Pub. Date: Oct. 3, 2013

(65) Prior Publication Data
US 2015/0050731 A1    Feb. 19, 2015

(30) Foreign Application Priority Data
Mar. 29, 2012    (JP) .................. 2012-077404

(51) Int. Cl.
| | | |
|---|---|---|
| C12N 5/071 | (2010.01) |
| C12N 5/02 | (2006.01) |
| C12N 5/00 | (2006.01) |
| C12N 5/074 | (2010.01) |
| A61K 35/32 | (2015.01) |
| C12N 5/0775 | (2010.01) |
| A61K 35/12 | (2015.01) |

(52) U.S. Cl.
CPC ............ *C12N 5/0607* (2013.01); *A61K 35/12* (2013.01); *A61K 35/32* (2013.01); *C12N 5/0664* (2013.01); *C12N 2533/52* (2013.01); *C12N 2533/54* (2013.01); *C12N 2535/00* (2013.01); *C12N 2535/10* (2013.01)

(58) Field of Classification Search
CPC .................................................... C12N 5/067
See application file for complete search history.

(56) References Cited

U.S. PATENT DOCUMENTS

| | | |
|---|---|---|
| 5,486,359 A | 1/1996 | Caplan et al. |
| 5,827,740 A | 10/1998 | Pittenger |
| 6,328,960 B1 | 12/2001 | McIntosh et al. |
| 6,387,369 B1 | 5/2002 | Pittenger et al. |
| 6,835,377 B2 | 12/2004 | Goldberg et al. |
| 2008/0299649 A1 | 12/2008 | Martin et al. |
| 2011/0002895 A1 | 1/2011 | Ueda et al. |

FOREIGN PATENT DOCUMENTS

| | | | |
|---|---|---|---|
| JP | 2004-129549 | 4/2004 | |
| JP | 2004-201612 | 7/2004 | |
| JP | 2004-210713 | 7/2004 | |
| JP | 2005-516616 | 6/2005 | |
| JP | 2006-238875 | 9/2006 | |
| JP | 2006280234 | 10/2006 | |
| JP | 2008-507962 | 3/2008 | |
| JP | 2008-295420 | 12/2008 | |
| JP | 2009-527223 | 7/2009 | |
| JP | WO2010/050626 | * 5/2010 | ............ C12N 15/09 |
| JP | 2010-252778 | 11/2010 | |
| JP | 2010-268715 | 12/2010 | |
| JP | 2011-177140 | 9/2011 | |
| JP | 2011-525798 | 9/2011 | |
| WO | 2002/007679 | 1/2002 | |
| WO | 2005/093044 | 10/2005 | |
| WO | 2009/057537 | 5/2009 | |
| WO | 2009/072527 | 6/2009 | |
| WO | 2009/156495 | 12/2009 | |

OTHER PUBLICATIONS

NIH (Stem Cells: Scientific Progress and Future Research Directions, Department of Health and Human Services, Chapter 1, pp. 1-4, Jun. 2001).*
Thomson et al. (PNAS, 92:7844-7848 (Aug. 1995).*
Perlea (Rom J Morphol Embryol 2016, 57(4):1187-1193).*
Liu (2006, Methods in Enzymology, 419:99-103).*
Sana (2017, Cytotechnology, 69:617-630).*
Katritsis et al, "Transcoronary transplantation of autologous mesenchymal stem cells and endothelial progenitors into infarcted human myocardium," Catheter Cardiovasc Interv. 65(3): 321-329 (2005).
Ringden et al., "Mesenchymal stem cells for treatment of therapy-resistant graft-versus-host disease" Transplantation. 81(10): 1390-1397 (2006).
Zhou et al., "Efficacy of bone marrow-derived mesenchymal stem cells in the treatment of sclerodermatous chronic graft-versus-host disease: clinical report," Biol Blood Marrow Transplant. 16(3): 403-412 (2007).
Morito et al., "Effects of basic fibroblast growth factor on the development of the stem cell properties of human dental pulp cells" Arch. Histol. Cytol., 2009, vol. 72, No. 1, pp. 51-64.
Suda et al., "The basic approach to lesion sterilization and tissue regeneration therapy (LSTR): effects of fibronectin and type I collagen on human pulpal cell adhesion" Nihon Shika Hozongaku Zasshi, 1997, vol. 40, No. 4, pp. 954-964 (English language abstract).

(Continued)

*Primary Examiner* — Valarie E Bertoglio
(74) *Attorney, Agent, or Firm* — Hamre, Schumann, Mueller & Larson, P.C.

(57) ABSTRACT

Disclosed is a method for producing pluripotent stem cell-enriched human dental pulp-derived cells. The method is characterized in that it includes (a) culturing a dental pulp suspension in a feeder cells-culture vessel containing feeder cells whose proliferative ability is suppressed, on a membrane having micropores that can block passage of the feeder cells and supported in the feeder cells-culture vessel in a manner to prevent the lower side face thereof from contacting with the feeder cells, thereby preventing direct contact with the feeder cells, and, (b) a step for recovering the cells proliferating on the membrane.

9 Claims, 2 Drawing Sheets

(56) References Cited

OTHER PUBLICATIONS

Haynes et al., "Glutamine prevents hydrogen peroxide-induced enterocyte death" Faseb J., 2004, vol. 18, No. 4, p. A476, 339.5.

Minamoto et al., "Development of a serum-free and heat-sterilizable medium and continuous high-density cell culture" Cytotechnology, 1991, vol. 5, p. S35-51.

Yalvac et al., "Isolation and characterization of stem cells derived from human third molar tooth germs of young adults: implications in neo-vascularization, osteo-, adipo- and neurogenesis" Parmacogenom. J., 2010, vol. 10, pp. 105-113.

Portmann-Lanz et al., "Placental mesenchymal stem cells as potential autologous graft for pre- and perinatal neuroregeneration" Am. J. Obster. Gynecol., 2006, vol. 194, pp. 664-673.

Pierdomenico et al., "Multipotent mesenchymal stem cells stem cells with immunosuppressive activity can be easily isolated from dental pulp," Transplantation, 2005, vol. 80, No. 6, pp. 836-842.

Ou et al., "Three-dimensional co-culture facilitates the differentiation of embryonic stem cells into mature cardiomyocytes" J. Cell. Biochem., 2011, vol. 112, pp. 3555-3562.

Sugawara et al., "Kesshoban yurai zoshoku inshi (PDGF) in okeru shizui kansaibo zoshoku sokushin kiko no kaimei" J. Oral. Biosci., 2011, vol. 53, Suppl., p. 149, P1-55.

Hirata et al., "Expression of multiple stem cell markers in dental pulp cells cultured in serum-free media", JOE, vol. 36, No. 7, Jul. 2010, p. 1139-1144, 6 pages.

Kerkis et al., "Stem Cells in Dental Pulp of Deciduous Teeth", Tissue Engineering, vol. 18, No. 2, 2012, p. 129-138, 10 pages.

Verfaillie, "Can human hematopoietic stem cell be cultured ex vivo," Stem Cells, 1994, vol. 12, pp. 466-476.

Abraham et al., "Propagation of human embryonic and induced pluripotent stem cells in an indirect co-culture system," Biochemical and Biophysical Research Communications, 2010, vol. 393, pp. 211-216.

Kosaki et al.,"Expression analysis of growth factor and protease after mitomycin C treatment in cultured subconjunctival fibroblasts", J Jpn Ophthlmol Soc, V. 104, P. 131 038 (2000), with machine translation.

* cited by examiner

METHOD FOR PRODUCING PLURIPOTENT STEM CELLS DERIVED FROM DENTAL PULP

TECHNICAL FIELD

The present invention relates to a pluripotent stem cell obtained from dental pulp, and in particular to a method for production of pluripotent stem cells derived from dental pulp possessing the ability to differentiate into chondrocytes and osteoblasts and the ability to suppress T cell proliferation as well.

BACKGROUND ART

Stem cells (pluripotent stem cells) having the ability to differentiate into cells of multiple lineages are known to be obtained from various tissues. Mesenchymal stem cells isolated from bone marrow are one of such groups of cells and have the ability to differentiate into various cells such as osteocytes, cardiomyocytes, chondrocytes, and adipocytes (Patent Documents 1 to 4). Using this differentiation ability, attempts have been made to apply mesenchymal stem cells in regenerative treatment of various tissues. For example, it has been reported that administration of mesenchymal stem cells to patients with myocardial infarction was tested aiming to regenerate the cardiac muscle cells which had undergone necrosis in myocardial infarction, resulting in an improvement of the patients' cardiac function (Non-patent Documents 1).

It has also been known that mesenchymal stem cells can suppress T-cell mediated immune responses when administered to the living body, and thus can be used as a pharmaceutical agent to suppress rejection reaction after transplantation (Patent Document 5). Focusing on the mesenchymal stem cells' suppressive effect on rejection reaction, clinical studies are being conducted to investigate the clinical efficacy of human mesenchymal stem cells on graft-versus-host disease (GVHD) occurring after bone marrow transplantation (Non-patent Documents 2 and 3). In those clinical studies, human mesenchymal stem cells allogeneic to the patients have been used.

Use of mesenchymal stem cells has also been advocated for angiogenesis, autoimmune diseases, inflammatory responses (in Alzheimer's disease, Parkinson's disease, stroke, brain cells damage, psoriasis, chronic dermatitis, contact dermatitis, arthritis including osteoarthritis, rheumatoid arthritis, and the like, inflammatory bowel disease, chronic hepatitis), cancer, allergic diseases, sepsis, trauma (burn, surgery, transplantation), inflammation of tissues and organs (cornea, lens, pigment epithelium, retina, brain, spinal cord, uterus during pregnancy, ovaries, testes, adrenal gland) (Patent Document 6). However, in this literature, the efficacy of the mesenchymal stem cells has been examined in vitro only, and in vivo efficacy of the mesenchymal stem cells has not been evaluated.

Mesenchymal stem cells isolated from bone marrow have high proliferation potency in artificial media, and like other cultured cells, they can be stored and supplied in frozen state (Patent Document 7). Therefore, in clinical trials of allogeneic human mesenchymal stem cells against GVHD, mesenchymal stem cells are supplied to medical institutions in a frozen state, and are thawed and used immediately before administration to the patients.

Mesenchymal stem cells (MSCs) are known to be obtained not only from bone marrow but also from various tissues such as adipose tissue (Patent Document 8), umbilical cord and placental tissues (Patent Document 9). Mesenchymal stem cells (or other similar cells) can also be obtained from various dental tissues such as dental pulp, dental follicle (Patent Document 14), dental sac (Patent Documents 15 and 20), dental papilla (Patent Document 16), periodontal ligament (Patent Document 17). These mesenchymal stem cells are supposed to generally possess the ability to differentiate into adipocytes.

Mesenchymal stem cells from dental pulp are obtained roughly following this procedure (Patent Document 19). Namely, a tissue obtained through crushing an extracted tooth is treated with type I collagenase and dispase, and cell clumps are removed by filtration to obtain a cell suspension. The cells then are allowed to proliferate in a culture flask using a DMEM medium containing 20% FBS. The cells which proliferated and adhered to the inner surface of the culture flask are detached by trypsin treatment and recovered. The cells thus recovered are the mesenchymal stem cells. A serum-free medium for culturing mesenchymal stem cells derived from dental pulp has also been reported (Patent Document 18).

Dental pulp is a loose fibrous connective tissue that occupies the dental pulp cavity of tooth, and is divided into coronal pulp and radicular pulp depending on their location. In addition, some pluripotent undifferentiated cells except mesenchymal stem cells may possibly occur in the dental pulp. Therefore, pluripotent stem cells derived from other undifferentiated cells than mesenchymal stem cells and having different characteristics from mesenchymal stem cells may possibly be obtained from dental pulp. This possibility is supported by a report stating that stem cells derived from dental pulp do not differentiate into adipocytes (Patent Document 11). Namely, it is considered that stem cells obtained from dental pulp include at least two types which are distinguished from each other based on their ability or inability to differentiate into adipocytes. It has also been reported that stem cells obtained from the dental pulp of deciduous teeth have different properties from those occurring in the dental pulp of permanent teeth in that they, for example, have higher proliferative ability and exhibit higher expression levels of FGF2, TGF-$\beta$, collagen I and collagen III compared with those obtained from dental pulp of permanent teeth (Patent Document 19). Further there is a report showing that pluripotent stem cells derived from dental pulp differ from bone marrow-derived mesenchymal stem cells in their property when induced to differentiate into osteoblasts (Patent Document 20).

PRIOR ART DOCUMENTS

Patent Documents

[Patent Document 1] U.S. Pat. No. 5,486,359
[Patent Document 2] U.S. Pat. No. 5,827,740
[Patent Document 3] U.S. Pat. No. 6,835,377
[Patent Document 4] U.S. Pat. No. 6,387,369
[Patent Document 5] U.S. Pat. No. 6,328,960
[Patent Document 6] WO 2005/093044
[Patent Document 7] WO 2009/057537
[Patent Document 8] Japanese Patent Application Publication No. 2004-129549
[Patent Document 9] Japanese Patent Application Publication No. 2004-210713
[Patent Document 10] Japanese Patent Application Publication No. 2010-252778
[Patent Document 11] WO 2002/007679

[Patent Document 12] Japanese Patent Application Publication No. 2008-507962
[Patent Document 13] WO 2009/072527
[Patent Document 14] Japanese Patent Application Publication No. 2009-527223
[Patent Document 15] Japanese Patent Application Publication No. 2005-516616
[Patent Document 16] Japanese Patent Application Publication No. 2006-238875
[Patent Document 17] Japanese Patent Application Publication No. 2008-295420
[Patent Document 18] Japanese Patent Application Publication No. 2011-177140
[Patent Document 19] Japanese Patent Application Publication No. 2010-268715
[Patent Document 20] Japanese Patent Application Publication No. 2004-201612

Non-Patent Documents

[Non-patent Document 1] Katritsis D G. et. al., Catheter Cardiovasc Interv. 65(3): 321-9 (2005)
[Non-patent Document 2] Ringden O. et. al., Transplantation. 81(10): 1390-7 (2006)
[Non-patent Document 3] Zhou H. et. al., Biol Blood Marrow Transplant. 16(3): 403-12 (2007)

SUMMARY OF INVENTION

Technical Problem

Against the above background, it is an objective of the present invention to provide a method for obtaining a cell population that contains pluripotent stem cells derived from human dental pulp at an increased proportion. It is another objective of the present invention to provide a method for obtaining a cell population that contains pluripotent stem cells derived from human dental pulp and having both of the abilities to differentiate into chondrocytes and osteoblasts and to inhibit T cell proliferation, at an increased proportion.

Solution to Problem

In a study directed to the above objectives, the present inventor found that the cells with high proliferative ability that were obtained by collecting cells from dental pulp and culturing them in the presence of feeder cells are pluripotent stem cells possessing both of the abilities to differentiate into chondrocytes and osteoblasts and to inhibit T cell proliferation, and completed the present invention based thereon. Thus, the present invention provides what follows.

(1) A method for production of pluripotent stem cell-enriched human dental pulp-derived cells comprising the steps of,
  (a) culturing dental pulp-derived cells contained in a dental pulp suspension in a feeder cells-culture vessel containing feeder cells whose proliferative ability is suppressed, on a membrane having micropores that can block passage of the feeder cells and supported in the feeder cells-culture vessel in a manner to prevent the lower side face thereof from contacting with the feeder cells, thereby preventing direct contact of the dental pulp-derived cells with the feeder cells, and
  (b) recovering the cells that have proliferated on the membrane.

(2) The method for production according to 1 above further comprising the steps that are conducted at least once and consists of,
  (c) culturing the recovered cells in a feeder cells-culture vessel containing feeder cells whose proliferative ability is suppressed, avoiding direct contact with the feeder cells, and on a membrane having micropores that can block passage of the feeder cells and supported in the feeder cells-culture vessel in order not to contact on the lower side face thereof with the feeder cells, and
  (d) recovering the cells that have proliferated on the membrane.

(3) The method for production according to 1 or 2 above, wherein the membrane is coated with fibronectin or collagen.

(4) The method for production according to one of 1 to 3 above, wherein the mean diameter of the micropores is 0.1 to 1.5 μm.

(5) The method for production according to one of 1 to 4 above, wherein the feeder cells are mammalian cells whose proliferative ability is suppressed by mitomycin C.

(6) The method for production according to 5 above, wherein the mammalian cells are NIH3T3 cells.

(7) The method for production according to one of 1 to 6 above, wherein the culture is conducted by using Dulbecco's modified Eagle medium that contains 10 to 25% of fetal bovine serum and 3 to 5 mM of L-alanyl-L-glutamine and whose glucose concentration is 5 to 7 mM.

(8) The method for production according to one of 1 to 6 above, wherein the culture is conducted by using Dulbecco's modified Eagle medium that contains 20% fetal bovine serum and 4 mM L-alanyl-L-glutamine and whose glucose concentration is 5.5 to 5.7 mM.

(9) The method for production of pluripotent stem cell-enriched human dental pulp-derived cells comprising the steps of: recovering the cells by the method for production according to one of 1 to 8 above; adding the recovered cells to a culture vessel at a density of 1000 to 20000 cells/cm$^2$; and culturing them until 70 to 100% of the bottom face of the culture vessel is occupied by the cells.

(10) The method for production of pluripotent stem cell-enriched human dental pulp-derived cells comprising the steps of: recovering the cells by the method for production according to one of 1 to 8 above; adding the recovered cells to a culture vessel at a density of 5000 to 10000 cells/cm$^2$; and culturing them until 90 to 100% of the bottom face of the culture vessel is occupied by the cells.

(11) The pluripotent stem cell-enriched human dental pulp-derived cells obtained by the method according to one of 1 to 10 above.

(12) The cells according to 11 above, wherein the cells are positive for the surface antigen markers CD29, CD44, CD73, CD90, CD105, and CD166, and negative for CD34 and CD45.

(13) The cells according to 12 above, wherein the cells possess the ability to differentiate into chondrocytes and osteoblasts, and also the ability to suppress T cell proliferation as well.

(14) The cells according one of 11 to 13 above, wherein the cells possess the ability to divide not less than 10 times.

(15) An immunosuppressive agent comprising the cells according to one of 11 to 14 above.

(16) T cell proliferation suppressive agent comprising the cells according to one of 11 to 14 above.

(17) A pharmaceutical agent for treatment of graft-versus-host-disease comprising the cells according to one of 11 to 14 above.

Advantageous Effects of Invention

The present invention enables efficient production of human dental pulp derived cells containing pluripotent stem cells at an increased proportion. Further, the pluripotent stem cells thereby obtained have the ability to differentiate into chondrocytes and osteoblasts and the ability to suppress T cell proliferation.

MODE FOR CARRYING OUT THE INVENTION

Figure 1:
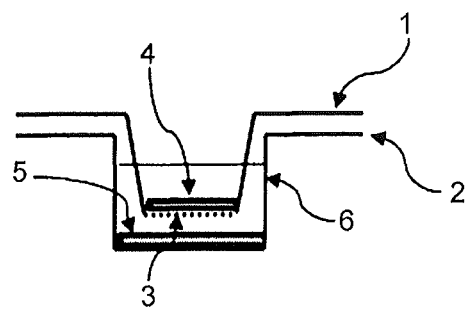
FIG. 1 A schematic diagram illustrating a setting of the culture vessel for P0 culture and pre-expansion culture.

In the present specification, the term "dental pulp" refers to the loose fibrous connective tissue that fills the dental pulp cavity of a tooth, which is made up of connective tissue containing blood vessels, nerves, and lymph vessels, and a layer of odontoblasts having the ability to deposit and repair dentin from inside. The dental pulp can be divided into the coronal pulp and the radicular pulp depending on the location, and the term "dental pulp" in the present invention includes at least either coronal pulp or radicular pulp.

In the present specification, a tooth extracted for preparing dental pulp is used preferably within 24 hours after tooth extraction, and more preferably 12 hours after tooth extraction. The dental pulp removed from the extracted tooth is minced with a tool such as a scissor, and then treated with a proteolytic enzyme. The proteolytic enzyme used for this is preferably a mixed solution of collagenase type II and dispase, and their concentrations are preferably 1 to 2 mg/mL and 3000 to 7000 units/mL, respectively, and more preferably about 1.5 mg/mL and about 5000 units/mL, respectively. The temperature for treatment with proteolytic enzyme is preferably 35 to 37° C., and the duration of the treatment is preferably for 1 to 3 hours. A dental pulp suspension then is prepared by disintegrating the proteolytic enzyme-treated dental pulp by pipetting. It is preferable to spin down the dental pulp suspension once to settle the cells for removing the enzyme along with the supernatant. The precipitate including cells, after removal of supernatant, are suspended again in a medium. The dental pulp suspension thus obtained contains not only the cells released from the dental pulp but also tissue debris of the dental pulp. In the present invention, the phrase "dental pulp-derived cells contained in a dental pulp suspension" means the cells combined with dental pulp debris contained in the dental pulp suspension.

In the present specification, the phrase "pluripotent stem cell-enriched human dental pulp-derived cells" refers to a population of the cells derived from human dental pulp where the proportion (proportion in number) of pluripotent stem cells is increased compared with cells collected directly from human dental pulp, and it includes isolated pluripotent stem cells finally obtained from human dental pulp through selection by means of culture or the like.

In the present invention, the term "feeder cells" refers to such cells that can be used in culturing dental pulp to promote the growth of the cells contained in the dental pulp. Feeder cells act to promote the growth of pluripotent stem cells by supplying nutrients and particular growth factors lacking in the medium. The feeder cells are treated before use so as to suppress their proliferative ability. Examples of methods for such a treatment include treatment with an agent that inhibits cellular DNA replication or X ray irradiation. As an agent that inhibits cellular DNA replication, mitomycin C can be preferably used. Though there is no particular limitation on which cells are to be employed as feeder cells as far as they can promote growth of the pluripotent stem cells contained in dental pulp, but preferred examples include NIH3T3 cells, BALB/3T3 cells, Swiss3T3, and mesenchymal stem cells, among which NIH3T3 cells are particularly preferred. Herein, examples of mesenchymal stem cells that can be used as feeder cells include human bone marrow-derived mesenchymal stem cells obtainable following the procedure disclosed in U.S. Pat. No. 5,486,359.

In the present invention, there is no particular limitation on the "feeder cells-culture vessel" to be used for culturing feeder cells, insofar as it can culture the mammalian cells, but such vessels are preferred that allow the cells to grow adhered to them. When NIH3T3 cells are used as feeder cells, the feeder cells added to the feeder cells-culture vessel adhere to the bottom of the vessel. There is no particular limitation on the shape of feeder cells-culture vessels, but a dish-typed vessel with a flat bottom is preferable. Examples of such dish-typed culture vessels with a flat bottom include commercially available 24 plate, 12 well plate, 6 well plate, and the like. The bottom of a feeder cells-culture vessel is preferably coated with a cell adhesive glycoprotein such as fibronectin, collagen (collagen type I, type IV, and the like), laminin, and the like, or a peptide containing the cell adhesion active site of these cell adhesive glycoprotein (RGD sequence).

Inside the feeder cells-culture vessel is attached a membrane that has micropores and can prevent passage of the feeder cells. The membrane is attached inside the feeder cells-culture vessel nearly horizontally relative to the bottom face of the culture vessel so that a sufficient space for culturing feeder cells is secured beneath it and its lower side face avoids contact with feeder cells. As the material of the membrane, polyethylene terephthalate and polycarbonate are preferable, and particularly preferred is polyethylene terephthalate. The micropores of the membrane is of such a pore size that blocks passage of the feeder cells (and preferably the pluripotent stem cells, too) but allows the dissolved components contained as solutes in the medium to pass through. The pore size of the micropores is preferably 0.1 to 1.5 μm, more preferably 0.2 to 1.2 μm, and further more preferably 0.4 to 1.0 μm. Because of their much bigger sizes than the pore size, the feeder cells (and also the pluripotent stem cells) cannot pass through the membrane even if they include some floating cells, whereas the medium and the dissolved components secreted from the feeder cells, such as growth factors, can pass through the membrane. The membrane is preferably pre-coated with fibronectin, collagen (collagen Type I, Type IV, and the like), and laminin, and the like.

Incubation is carried out after addition of the above-described dental pulp suspension on this membrane. During the incubation, the medium is added to the vessel as needed so as to ensure that the cells contained in the dental pulp suspension added on the membrane are completely covered with the medium. Thus, the incubation is carried out with the dental pulp suspension placed on the upper side and the feeder cells on the lower side (but without contacting the membrane) of the interposed membrane. During the incubation, components such as growth factors derived from the feeder cells are supplied also to the upper side of the membrane through the micropores of the membrane. In addition, components secreted from the tissue debris contained in the dental pulp suspension also join the medium. Thus it is not preferable to pass the dental suspension through a mesh to remove the tissue debris when preparing a dental pulp suspension as disclosed, e.g., in Patent Documents 10 and 19, for the tissue debris also, as with the feeder cells, may supply with such nutrients and unique growth factors as lacking in the medium.

Culture medium used in culturing of the dental pulp is preferably Dulbecco's modified Eagle medium containing 10-25% fetal bovine serum, 3-5 mM L-alanyl-L-glutamine, and 5-7 mM D-glucose, and more preferably Dulbecco's modified Eagle medium containing 20% fetal bovine serum, 4 mM L-alanyl-L-glutamine, and 5.5-5.7 mM D-glucose. Table 1 shows an example of the detailed composition of a medium. Each component can be replaced with its equivalent.

TABLE 1

Formulation of Dulbecco's modified Eagle medium

| Components | mM (Range) | mM (Range) |
| --- | --- | --- |
| Glycine (aminoacetic acid) | 0.2-0.6 | 0.4 |
| L-Arginine hydrochloride | 0.3-0.5 | 0.398 |
| L-Cystine dihydrochloride | 0.15-0.25 | 0.201 |
| L-Glutamine | 3-5 | 4 |
| L-Histidine hydrochloride monohydride | 0.15-0.25 | 0.2 |
| L-Isoleucine | 0.65-0.95 | 0.802 |
| L-Leucine | 0.65-0.95 | 0.802 |
| L-Lysine hydrochloride | 0.65-0.95 | 0.798 |
| L-Methionine | 0.15-0.25 | 0.201 |
| L-Phenylalanine | 0.2-0.6 | 0.4 |
| L-Serine | 0.2-0.6 | 0.4 |
| L-Threonine | 0.65-0.95 | 0.798 |
| L-Tryptophan | 0.06-0.1 | 0.0784 |
| L-Tyrosine disodium dihydrate | 0.2-0.6 | 0.398 |
| L-Valine | 0.65-0.95 | 0.803 |
| Choline chloride | 0.02-0.04 | 0.0286 |
| D-Calcium pantothenate | 0.007-0.009 | 0.00839 |
| Folic acid | 0.008-0.01 | 0.00907 |
| Nicotinamide | 0.03-0.05 | 0.0328 |
| Pyridoxine hydrochloride | 0.015-0.025 | 0.0196 |
| Riboflavin | 0.0008-0.0012 | 0.00106 |
| Thiamine hydrochloride | 0.01-0.014 | 0.0119 |
| i-Inositol | 0.03-0.05 | 0.04 |
| Calcium chloride (anhydrous) | 1.5-2.1 | 1.8 |
| Ferric nitrate nonahydrate | 0.0002-0.0004 | 0.000248 |
| Magnesium sulfate | 0.65-0.95 | 0.814 |
| Potassium chloride | 5-6 | 5.33 |
| Sodium bicarbonate | 40-48 | 44.05 |
| Sodium chloride | 100-120 | 110.34 |
| Sodium dihydrogen phosphate monobasic-水和物 | 0.65-0.95 | 0.906 |
| D-Glucose | 5-7 | 5.56 |
| Phenol red | 0.03-0.05 | 0.0399 |
| Sodium pyruvate | 0.8-1.2 | 1 |

In the present specification, the culture that is started after addition of the dental pulp suspension onto the membrane attached inside the feeder cells-culture vessel is referred to as "primary culture (P0)" of the dental pulp-derived cells. The primary culture (P0) is preferably carried out until a colony formed by cell proliferation on the membrane can be observed with naked eyes. During the primary culture (P0), it is not required to use the original feeder cells, but the primary culture may be carried out replacing the feeder cells, for example, by transferring the membrane, together with the cells and the issue debris on it, to a fresh feeder cells-culture vessel. When the feeder cells come to detach from the bottom face of the feeder cells-culture vessel during the culture, it is desirable to perform such a transfer.

When colonies are observed forming on the membrane, the membrane is washed (with a washing solution such as a proper medium, either identical to or different from the medium used for the culture, a buffer solution which has no risk of adversely influencing on the cells, and so on) to remove floating cells and tissue debris, and the cells that formed colonies are recovered by detaching them from the surface of the membrane. Recovery of the cells may be performed by a conventional method as in the case of recovery of cultured cells adhered to the container in general, namely, by adding proteolytic enzyme, such as trypsin, detaching and dispersing the cells that formed colonies from the membrane, and terminating the enzyme reaction by a conventional method. The cells thus recovered then are added again to the membrane and cultured in the feeder cells-culture vessel, in the same manner as the P0 culture (but without inclusion of dental pulp debris). In the present specification, this culture is referred to as "pre-expansion culture" of dental pulp-derived cells. Pre-expansion culture is preferably performed at least once.

In the primary culture (P0) and the pre-expansion culture, pluripotent stem cells multiply on the membrane most actively among the dental pulp-derived cells. Therefore, by recovering the cells proliferating on the membrane, pluripotent stem cell-enriched human dental pulp-derived cells can be obtained, which is a population of cells containing a greatly increased proportion of pluripotent stem cells compared with other cells originally contained in human dental pulp.

Moreover, every time when the pre-expansion culture (or the below-mentioned expansion culture) is repeated, the proportion of pluripotent stem cells contained in the recovered pluripotent stem cell-enriched human dental pulp-derived cells is rapidly increased because of the greater multiplication rate of the pluripotent stem cells. Thus, isolated pluripotent stem cells can be obtained by repeating culture cycles.

When a pre-expansion culture is performed multiple times, each culture is performed after addition of the cell suspension that is obtained by recovering the colonies formed on the membrane in the preceding cycle of pre-culture onto a fresh membrane in a fresh feeder cells-culture vessel. There is no particular upper limitation on how many cycles of pre-expansion culture is conducted. As it is enough that pluripotent stem cell-enriched human dental pulp-derived cells are obtained in an amount for use in the below-mentioned expansion culture, repetition of about 2 to 5 times will be generally sufficient even if performed multiple times.

After a sufficient number of pluripotent stem cell-enriched human dental pulp-derived cells are obtained, the cells can be subjected to an expansion culture, and the expansion culture can be repeated until a necessary number of pluripotent stem cell-enriched human dental pulp-derived cells are obtained.

In the present specification, the term "expansion culture" refers to a culture carried out in the absence of feeder cells to increase the number of pluripotent stem cell-enriched human dental pulp-derived cells (in particular, pluripotent stem cells). Pluripotent stem cells, in general, begin to actively grow even in the absence of feeder cell if the cell density in a culture vessel at the start of cell culture exceeds a certain level. Such cell density, is at least 500 cells/cm$^2$ in many cases, preferably not less than 1000 cells/cm$^2$, more preferably not less than 3000 cells/cm$^2$, and still more preferably not less than 5000 cells/cm$^2$. The cell density here can be calculated by dividing the number of living cells in the cell suspension seeded in the culture vessel at the start of the expansion culture by the area of the bottom face of the culture vessel.

In expansion culture, pluripotent stem cells are allowed to attach to the culture vessel and grow there. Thus, a culture vessel used in expansion culture is that which permits culture of mammalian cells adhered thereto, whose bottom is preferably coated with a cell adhesion glycoprotein such as fibronectin, collagen (e.g., collagen type I, type IV), laminin and the like, or a peptide containing the cell adhesion active site of such a cell adhesion glycoprotein (RGD sequence). Commercially available culture vessels for animal cell can be used as such vessels. There is no particular limitation on the shape of a culture vessel used in expansion culture so long as it allows the cells to be cultured while adhering to it. Though a flat-bottomed dish type is preferable, a roller bottle type may also be used.

In expansion culture, the cells are seeded in the culture vessel so that the cell density at the start of culture is preferably 1000 to 20000 cells/cm$^2$, more preferably 3000 to 15000 cells/cm$^2$, further more preferably 5000 to 10000 cells/cm$^2$. And the culture is continued either until the proportion of the bottom face of the culture vessel occupied by cells reaches preferably to 70 to 100%, more preferably to 80 to 100%, and still more preferably to 90 to 100%, or preferably for 5 to 10 days, more preferably for 6 to 8 days, and still more preferably for 7 days. The cells thus cultured then are recovered from the culture vessel by treatment with trypsin or the like. The expansion culture is repeated until the number of recovered cells reaches a desired amount. Pluripotent stem cells proliferate most actively in expansion culture, too, and therefore the cells obtained by expansion culture come to consist substantially of pluripotent stem cells only. When observed in the state still adhering to the culture vessel, pluripotent stem cells obtained by the expansion culture preferably exhibit a homogeneous spindle-like shape.

In the present invention, the term "pluripotent stem cell" refers to a cell that has both the abilities to proliferate and differentiate into at least two cell types. Human dental pulp-derived pluripotent stem cells obtained by the present invention preferably has the ability to differentiate into osteoblasts and chondrocytes. Further, human dental pulp-derived pluripotent stem cells obtained in the present invention are basically positive for CD29, CD44, CD73, CD90, CD105 and CD166, and negative for CD34 and CD45.

In the expansion culture carried out in the present invention, human dental pulp-derived pluripotent stem cells have been confirmed to divide not less than 40 times from the start of culture (see Examples). Thus, for example, it is possible to obtain theoretically about $1\times10^{12}$ or more cells from a single pluripotent stem cell. Considering that an extracted tooth, the source material, is obtainable with relative ease, pluripotent stem cells having such a high ability to divide are promising as a supply source of pluripotent stem cells compared with other pluripotent stem cells such as bone marrow-derived mesenchymal stem cells. However, the proliferative ability of pluripotent stem cells decreases as they divide repeatedly. Therefore, when the pluripotent stem cells having particularly high proliferative ability are needed, the number of expansion culture cycles performed is preferably 12 times or less, more preferably 10 times or less, and most preferably five times or less.

Dental pulp-derived pluripotent stem cells obtained through proliferation according to the present invention have the ability to differentiate into osteoblasts and chondrocytes. Therefore, the pluripotent stem cell-enriched human dental pulp-derived cells (including human dental pulp-derived pluripotent stem cells finally isolated) can be used in diseases involving destruction of bone and cartilage tissue as a therapeutic agent for promoting their regeneration. As the pluripotent stem cells have the ability to inhibit T cell proliferation, and thus have an immunosuppressive activity, the pluripotent stem cell-enriched human dental pulp-derived cells can also be used as a T cell proliferation inhibiting agent and an immunosuppressive agent. When the cells are used as a T cell proliferation inhibiting agent or an immunosuppressive agent, the target diseases include, for example, autoimmune diseases (Guillain-Barre syndrome, autoimmune pancreatitis, insulin-dependent diabetes mellitus, rheumatoid arthritis, and systemic lupus erythematosus, and the like), graft-versus-host disease and the like.

When used as a therapeutic agent, the pluripotent stem cell-enriched human dental pulp-derived cells in the present invention are administered, as a suspension, in the form of an intravenous drip or locally injected. In addition, the cells can be administered not only to the very person that provided the dental pulp, but also to other persons than the provider of the dental pulp.

If heterologous administration is envisaged, the pluripotent stem cell-enriched human dental pulp-derived cells of the present invention can be produced in a large amount by using two or more extracted tooth obtained from two or more donors, and then can be frozen stored. In this case, a manufacturer, such as a pharmaceutical company, can produce a large number of these cells, frozen store them, and can provide them as a therapeutic agent upon request of medical institutions. Frozen pluripotent stem cell-enriched human dental pulp-derived cells are thawed in medical institutions and administered to patients.

EXAMPLES

While the present invention will be described in further detail below referring to examples, it is not intended that the present invention be limited to the examples.

[Feeder Cell Preparation]

FBS and L-alanyl-L-glutamine were added to DMEM Low Glucose (Invitrogen Inc.) at the concentration of 10% and 4 mM, respectively, and the medium thus prepared was designated DMEM (10% FBS) medium. Mitomycin C (SIGMA) was dissolved to the concentration of 0.2 mg/mL in water for injection, and the solution thus prepared was designated Mitomycin C solution. FBS (Invitrogen Inc.) and L-alanyl-L-glutamine were added to DMEM Low Glucose (Invitrogen Inc.) at the final concentration of 20% and 4 mM, respectively, and the medium thus prepared was designated DMEM (20% FBS).

NIH3T3 cells frozen stored in liquid nitrogen were taken out and thawed in a thermostatic bath set to 37° C. The cells then were added with DMEM (10% FBS) medium and suspended in it, and was centrifuged (1500 rpm, 5 min). The supernatant was discarded, and the cells were suspended in DMEM (10% FBS) medium, seeded in a 75 cm$^2$ culture flask, and incubated at 37° C. under 5% $CO_2$ until the cell density reached 80 to 90%. The cells were washed with Dulbecco's phosphate buffered solution (D-PBS, Invitrogen Inc.), and then a medium prepared by adding 0.4 mL of Mitomycin C solution to 9.6 mL of DMEM (10% FBS) medium was added to the culture flask, and the cells were left undisturbed at 37° C. under 5% $CO_2$. After removal of the medium, the cells were washed with D-PBS, and after addition of 1 mL solution of a 0.25% trypsin-EDTA solution, left undisturbed for 5 to 10 minutes at 37° C. After confirming the detachment of cells, the reaction was stopped by addition of DMEM (10% FBS) medium. After the cells were suspended, the number of viable cells was counted on a hemacytometer. The cells were collected in a 15 mL centrifuge tube, precipitated by centrifugation (1500 rpm, 5 min), and suspended at the cell density $1 \times 10^6$ cells/mL in a serum solution containing 10% DMSO (v/v), and dispensed 2 ml each into cryopreservation tubes, and then were frozen at −80° C. After stored at −80° C. for more than 24 hours, the cells were transferred into liquid nitrogen for storage. Frozen cells thus obtained were used as feeder cells.

Before use, the frozen feeder cells were taken out from the liquid nitrogen and thawed, and after suspended in DMEM (20% FBS) medium that was added, precipitated by centrifugation (1500 rpm, 10 min). And then the cells were suspended in DMEM (20% FBS) medium at a concentration of $4 \times 10^4$ cells/mL, and the suspended feeder cells were added 500 μL each to the bottom wells of 12-well cell culture insert companion plate (12-well Companion Plate, BD Biosciences) so as to let the cells adhere to the bottom of the well.

[Isolation of Dental Pulp]

After 12 mg of collagenase type II (CALBIOCHEM) was added to 4 ml of D-PBS and mixed, the mixture was filtered through a 0.22 μm filter. The solution thus obtained was designated Collagenase Solution. After 10000 units of dispase (GODO SHUSEI CO., LTD) was added to 1 ml of D-PBS and mixed, the mixture was filtered through a 0.22 μm filter. The solution thus obtained was designated Dispase Solution.

An extracted tooth obtained based on an informed consent was transferred to a 10 cm dish after washing gently with Ringer's solution. The extracted tooth was washed with saline added to the dish, and after addition of a 0.5% chlorhexidine solution, shaken to sterilize the surface of the tooth. The extracted tooth then was placed under a sterile environment, and washed with sterilized saline until the 0.5% chlorhexidine is sufficiently removed. After removing the saline, the dental pulp was exposed by dividing the extracted tooth using sterilized dental pliers and forceps. After resected with surgical scissors, the dental pulp was transferred to a centrifuge tube and minced with surgical scissors. And then after addition of Collagenase Solution and Dispase Solution, 150 μl each, to the centrifuge tube, the dental pulp tissue was sufficiently disintegrated by pipetting, and was left undisturbed for 1 to 2 hours under 37° C.

Subsequently, the enzyme reaction was stopped by addition of 5 mL of DMEM (20% FBS) medium, and the cells were precipitated by centrifugation (1500 rpm, 10 min). After removal of the supernatant, the precipitate was suspended in 5 mL of DMEM (20% FBS) medium added and were again centrifuged (1500 rpm, 10 min) to precipitate the cells. After addition of 500 μL of DMEM (20% FBS) medium, the precipitate was suspended well by pipetting, and a suspension of dental pulp-derived cells containing tissue debris was obtained.

[Primary Culture (P0) of Dental Pulp-Derived Cells]

Fibronectin was added at a density of 1 μg/cm² to polyethylene terephthalate porous membrane having a pore size of 0.4 μm (track etched membrane) provided on the bottom face of 12-well insert (BD Falcon Cell Culture Insert, BD Biosciences), and then porous membrane was left undisturbed at 37° C. at least for 30 minutes to coat the membrane with fibronectin. Fibronectin was prepared by the method described in Horwitz B. et al, Preparation of fibronectin for therapeutic administration In:. Mosher D F, editor. New York Academic Press Inc 441-445 (1989).

The 12-well inserts coated with fibronectin was placed in the 12-well companion plate whose bottom wells contained the feeder cells as prepared above, and the dental pulp suspension (about 500 μL) was added onto this 12-well insert, and after DMEM (20% FBS) medium was further added so that all the cells were covered with the medium, the primary culture (P0) was started at 37° C. under 5% $CO_2$. FIG. 1 shows schematically the setting of the culture vessel for this. With medium exchanged every 3 to 4 days, the culture was continued until a colony has been visually confirmed on the 12-well insert. During this period, if the feeder cells in the bottom wells markedly detached from the bottom face of the bottom wells, a fresh 12-well companion plate was prepared containing feeder cells that adhered to the bottom face of its bottom wells, and the 12-well insert was transferred to this plate, where the culture was continued.

A 12-well insert on which a colony was visually confirmed was transferred to another companion plate, and the 1 ml of PBS was added to it to wash the cells that adhered to the 12-well insert and also to remove floating cells and tissue debris. 500 μL of 0.25% trypsin-EDTA solution was added to the 12-well insert, which then was left undisturbed for 5-10 minutes at 37° C. to detach the cells that had adhered to the porous membrane in the 12-well insert. Then, 300 μL of DMEM (20% FBS) medium was added to terminate the reaction and suspend the cells in it, and the cell suspension was collected in a centrifuge tube. And then, 300 μL each of DMEM (20% FBS) medium was added to the 12-well insert for suspending the remaining cells, which were collected in the same centrifuge tube. The collected cells were precipitated by centrifugation (1500 rpm, 5 min), and after removing the supernatant, 1 ml of DMEM (20% FBS) medium was added to form a cell suspension.

[Pre-Expansion Culture of Dental Pulp-Derived Cells]

A 6-well companion plate containing the feeder cells added to its bottom wells was prepared, and a 6-well insert coated with fibronectin then was placed in it. The cell suspension obtained by the primary culture (P0) was added to the 6-well insert, and pre-expansion culture was started at 37° C. in the presence of 5% $CO_2$. The setting of the culture vessel for this is schematically illustrated in FIG. 1. With DMEM (20% FBS) medium exchanged every 3 to 4 days, the culture was continued until a colony has been visually confirmed on the 6-well insert. During this period, if the feeder cells in the bottom wells markedly detached from the bottom wells, a fresh 6-well companion plate was prepared containing feeder cells that adhered to the bottom face of its bottom wells, and the 6-well insert was transferred to this plate, where the culture was continued.

The 6-well insert on which a colony was visually confirmed was transferred to another companion plate, and the cells were washed with PBS, and 500 μL of 0.25% trypsin-EDTA solution was added. After leaving the cells undisturbed for 5-10 minutes at 37° C. and confirming detachment of the cells, 500 μL of DMEM (20% FBS) medium was added to terminate the reaction and suspend the cells in it, and the cell suspension was collected in a centrifuge tube. And then, the wells were washed with 500 μL of DMEM (20% FBS) medium, and the washings were collected to the same centrifuge tube. The collected cells were precipitated by centrifugation (1500 rpm, 5 min), and after removing the supernatant, 500 μL of DMEM (20% FBS) medium was added to suspend the cells.

[Expansion Culture of Dental Pulp-Derived Cells]

After the number of viable cells contained in the above cell suspension was measured on a hemacytometer, the cells were seeded at a density of 5000 to 10000 cells/cm$^2$ in a culture flask, and expansion culture was started using DMEM (10% FBS) medium. However, if expansion culture cannot be started because the number of viable cells was too small, pre-expansion culture was repeated until the number of cells needed to start the expansion culture was obtained. The cells seeded in the culture flask at the start of expansion culture were observed and almost all the cells were found adhered to the bottom face of the culture flask and exhibited a spindle-like shape, confirming that homogeneous cells had been isolated.

After the cells were cultured in DMEM (10% FBS) medium until 90 to 100% cell confluency w as achieved, the cells were washed with PBS, and added with 0.25% trypsin-EDTA, and then were left undisturbed for 5 to 10 minutes at 37° C. to be detached. DMEM (10% FBS) medium was added to suspend the detached cells and stop the reaction, and the cell suspension was collected to a 15 ml centrifuge tube. The cells thus collected were precipitated by centrifugation (1500 rpm, 5 min), and after removing the supernatant, the cells were suspended in DMEM (10% FBS) medium. After measuring the number of viable cells on a hemacytometer, the cells were seeded at a density of 5000 to 10000 cells/cm$^2$ in a culture flask and cultured in DMEM (10% FBS) until 90 to 100% cell confluency was achieved. Expansion culture was repeated 16 times, and the number of cell division cycles was calculated based on the number of the cells measured at the end of each subculture. Besides, even if the cell confluency did not reach 90 to 100%, the cells were collected and subjected to the next expansion culture when seven days had elapsed from the start of each expansion culture. The proliferation rate of cells gradually decreased after the fourth expansion culture, and the cell confluency did not reach 90 to 100% even if seven days had elapsed from the start of each expansion culture

[Frozen Storage of from Dental Pulp-Derived Cells]

A portion of the cells cultured until the cell confluency reached 90-100% in the second expansion culture was frozen stored by the following method. After washing the cells with PBS, 0.25% trypsin-EDTA was added and the cells were left undisturbed for 5 to 10 minutes at 37° C. to be detached. DMEM (10% FBS) medium was added to stop the enzyme reaction and suspend the cells, and the cells then were collected to a 15 mL centrifuge tube. The cells thus collected were precipitated by centrifugation (1500 rpm, 5 min), and the supernatant was removed. The cells were suspended in a FBS solution containing 10% (v/v) DMSO at a density of 1×10$^6$ cells/mL. 0.5 to 2 mL each of the cell suspension was dispensed into a cryotube, and was placed in a BICELL (Japan freezer) that had been cooled at 4° C. in advance, and was frozen at −80° C. About 24 hours after freezing, the cells were transferred to vapor-phase liquid nitrogen and stored in it.

[Measurement of Proliferative Ability of Dental Pulp-Derived Cells]

Figure 2:
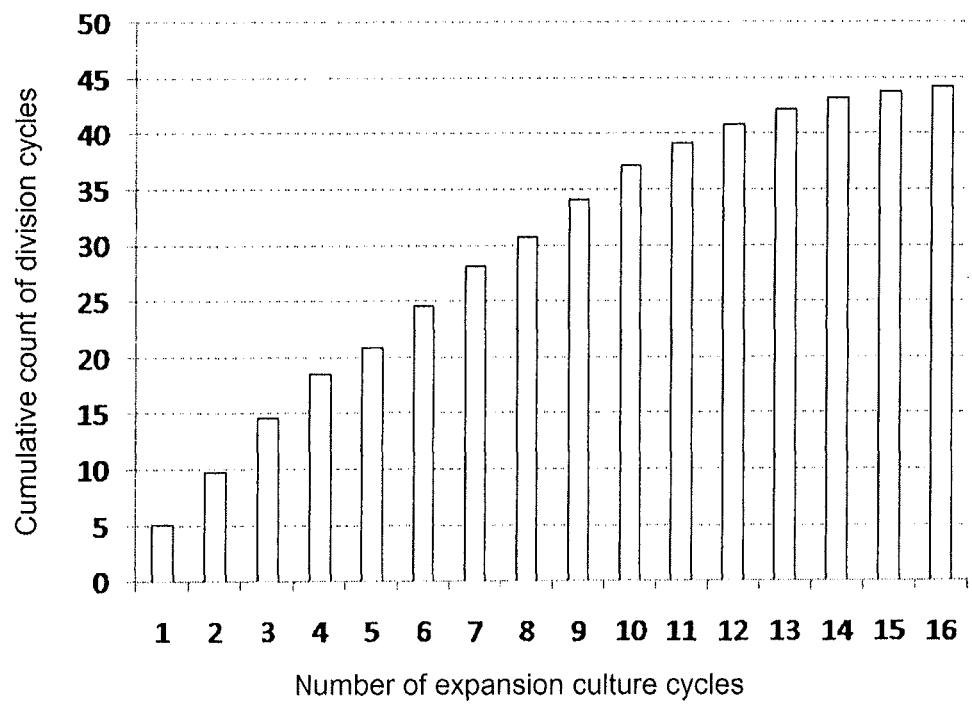
FIG. 2 A figure showing the proliferative ability of the pluripotent stem cell-enriched human dental pulp-derived cells in the course of expansion culture. Vertical axis: cumulative count of cell division cycles (times) in the expansion culture, horizontal axis: number of repetition of expansion culture cycles.

Subculture was repeated 16 times during the above expansion culture, and proliferative ability of the cells was determined by measuring the number of viable cells at the end of each subculture and calculating the number of cell division cycles (FIG. 2). The number of cell division cycles was calculated by the following formula from the number of viable cells at the start of each subculture and the number of viable cells at the end of the culture. In doing this, the culture at the start of the expansion culture was referred to as the first expansion culture. Thereafter, according to number of repeated subculture, the culture was referred to as the 2nd expansion culture, the 3rd expansion culture, and so on, and the last expansion culture thus was referred to as the 16th expansion culture.

Number of cell division cycles=log$_2$(number of the cells at the end of each culture/number of the cells at the start of each culture)

In the course of three consecutive expansion cultures (from the first to the third expansion cultures), the number of cells was increased by 2.67×10$^4$ times compared to that at the start of the expansion culture. Therefore, the total number of cell division at the end of the third expansion culture was about 14.7 cycles from the start of the expansion culture, and during this period the average number of cell division in each expansion culture was calculated about 4.9 cycles. Proliferative ability of cells was slightly decreased since the fourth expansion culture, and during seven consecutive expansion cultures (from the fourth to the 10th expansion cultures), the number of cells increased by 5.51× 10$^6$ times. Therefore, the total number of cell division at the end of the 10th expansion culture was about 22.4 cycles from the start of 4th expansion culture, and during this period the average number of cell division in each expansion culture was calculated about 3.2 cycles. The total number of cell division from the start of expansion culture was calculated about 37.1 cycles, therefore the number of cells was theoretically increased by about 1.47×10$^{11}$ times at the end of the 10th expansion culture compared to that at the start of expansion culture. Proliferative ability of cells was further decreased since the 11th expansion culture, and cell division almost stopped at the 16th expansion culture. During six consecutive expansion cultures (from the 11th to the 16th expansion cultures), the number of cells increased by 1.47× 10$^2$ times. The total number of cell division at the end of the 16th expansion culture was about 7.2 cycles from the start of 11th expansion culture, therefore during this period, the average number of cell division in each expansion culture was calculated about 1.2 cycles. The total number of cell division from the start of the expansion culture amounted to about 44.3 cycles, and the number of cells in culture was theoretically increased by about 2.16×10$^{13}$ times at the end of the 16th expansion culture from the start of expansion culture.

As the number of cells could not be accurately measured, the number of cell division cycles in P0 culture and pre-expansion culture was unknown. However, assuming that a colony detectable by visual inspection contained about 1000 cells, the number of cell division required for the formation of a colony is five cycles in the P0 and pre-expansion culture, respectively, and the number of cell division from the start of P0 culture to the end of the 16th expansion culture was estimated 54 cycles or more. This result indicates that the dental pulp-derived cells obtained by the method described above have an extremely high proliferative capacity.

[Measurement of Surface Antigens]

The dental pulp-derived cells showed a homogeneous spindle-shape similar with mesenchymal stem cells. Thus, FACS analysis was used to determine the presence or absence of expression of the surface antigens known to be positive, i.e. CD29, CD44, CD73, CD90, CD105 and CD166, and the surface antigens known to be negative, i.e. CD34 と CD45, on human mesenchymal stem cells.

Phosphate buffered saline, pH 7.4, contains BSA, (powder (Sigma Co.)) was dissolved in purified water, and filtrated through a 0.22 μm filter. The solution thus obtained was used as PBS-B [0.01M phosphate buffered saline containing 0.138 M sodium chloride, 0.0027 M KCl, and 1% (w/v) bovine serum albumin (pH 7.4)]. IgG from human (Sigma Co.) was dissolved in physiological saline (Otsuka Pharmaceutical Co., Ltd.), and the mixture was filtrated through a 0.22 μm filter to prepare 25 mg/mL IgG solution. Blocking solution was prepared by adding 0.4 mL of 25 mg/mL IgG solution to 4.6 ml of PBS-B. Streptavidin APC diluted solution was prepared by adding 0.4 mL of Streptavidin APC (CALTAG Co.) to 2.4 ml of PBS-B.

Diluted antibody solution of labeled antibody was prepared as follows. 2 μL of biotin-labeled mouse IgG1 isotype control (CALTAG Co.) was added 18 μL of PBS-B, and the solution thus obtained was used as diluted solution of biotin-labeled mouse IgG1 (IgG1-biotin diluted solution). 2 μL of biotin-labeled mouse anti-human CD90 antibody (BD Co.) was added to 38 μL of PBS-B, and the solution thus obtained was used as anti-CD90-Biotin diluted solution. 3.5 μL of biotin-labeled mouse anti-human CD166 (Fitzgerald Co.) was added to 46.5 μL of PBS-B, and the solution thus obtained was used as anti-CD166-Biotin diluted solution. As for FITC-labeled anti-human CD29 antibody (anti-CD29-FITC, BD Co.), FITC-labeled anti-human CD34 antibody (anti-CD34-FITC, BD Co.), biotin-labeled anti-human CD44 antibody (anti-CD44-Biotin, BD Co.), FITC-labeled anti-human CD45 antibody (anti-CD45-FITC, IMMUNOTECH Co.), PE-labeled anti-human CD73 antibody (anti-CD73-PE, BD Co.), PE-labeled anti-human CD105 antibody (anti-CD105-R-PE, Ancell Co.), FITC-labeled mouse IgG1 (anti-IgG1-FITC, IMMUNOTECH Co.), PE-labeled mouse IgG1 isotype control (IgG1-PE, IMMUNOTECH Co.), and biotin-labeled mouse IgG2b isotype control (IgG2b-biotin, BD Co.), commercially available products were directly used as the diluted antibody solution.

[Method for Cell Surface Staining]

The aforementioned frozen cells ($1\times10^6$ cells/mL) were thawed, and, the cells were gently mixed with 10 ml of DMEM (10% FBS) medium added, and then precipitated by centrifugation (1500 rpm, 5 min). The supernatant was discarded, the cells were suspended in 10 ml of DMEM (10% FBS) medium added, and again precipitated by centrifugation (1500 rpm, 5 min). Then, the cells were suspended in DMEM (10% FBS) medium, seeded to a culture vessel at a cell density of 5000 to 10000 cells/cm$^2$, and cultured in DMEM (10% FBS) medium until the cell confluency reached 90 to 100%. The cells were washed with PBS, and added with 0.25% trypsin-EDTA, and then left undisturbed for 5 to 10 minutes at 37° C. to be detached. The cells were suspended by addition of DMEM (10% FBS) medium, and the number of viable cells were counted. The dental pulp-derived cells ($2\times10^7$ cells) were collected in a 50 mL centrifuge tube and added with PBS-B to make the total volume of 28 mL. The cells were precipitated by centrifugation (1500 rpm, 5 min) and the supernatant was discarded. And then the cells were suspended in 700 μL of blocking solution and left undisturbed on the ice for 20 min. Each of the diluted antibody solutions was added to each of 5 mL reaction tubes (number (1) to (13), total 13 tubes) as shown in Table 2. Then, 50 μL of cell suspended in blocking solution were added to each tube and mixed gently and then left undisturbed on ice for 20 minutes let the antibody contained in the reagent bind to the surface antigen markers expressed on the cell surface. Then, the cells were added with 3 mL of PBS-B and mixed, and then precipitated by centrifugation (1500 rpm, 5 min) and the supernatant was discarded to remove the antibodies that did not bind to the cells. This step for removing antibodies was repeated once.

TABLE 2

The type and amount of diluted antibody solution added to each reaction tube

| Tube number | Diluted antibody solution | Volume of Additive |
|---|---|---|
| (1) | PBS-B | 50 μL |
| (2) | IgG1-FITC | 20 μL |
| (3) | IgG1-PE | 20 μL |
| (4) | IgG1-biotin diluted solution | 10 μL |
| (5) | IgG2b-biotin | 20 μL |
| (6) | Anti-CD29-FITC | 20 μL |
| (7) | Anti-CD34-FITC | 20 μL |
| (8) | Anti-CD44-biotin | 20 μL |
| (9) | Anti-CD45-FITC | 20 μL |
| (10) | Anti-CD73-PE | 20 μL |
| (11) | Anti-CD90-biotin diluted solution | 10 μL |
| (12) | Anti-CD105-R-PE | 5 μL |
| (13) | Anti-CD166-biotin diluted solution | 15 μL |

Then, after a staining reagent was added to each reaction tube as shown in Table 3 and mixed, the tubes were allowed to stand for 15 min on ice. 3 ml of PBS-B then was added to each reaction tube and mixed gently, and the cells were precipitated by centrifugation (1500 rpm, 5 min), and the supernatant was removed. 3 mL of PBS-B was again added to each reaction tube, and after the cells were suspended, the cells were precipitated by centrifugation (1500 rpm, 5 min), and the supernatant was removed. This step for cell washing was repeated once more.

TABLE 3

The type and amount of staining reagent that was added to each reaction tube

| Tube number | Staining reagent | Volume Added |
|---|---|---|
| (1) | PBS-B | 50 μL |
| (2) | PBS-B | 50 μL |
| (3) | PBS-B | 50 μL |
| (4) | Streptavidin APC diluted solution | 50 μL |
| (5) | Streptavidin APC diluted solution | 50 μL |
| (6) | PBS-B | 50 μL |
| (7) | PBS-B | 50 μL |
| (8) | Streptavidin APC diluted solution | 50 μL |
| (9) | PBS-B | 50 μL |
| (10) | PBS-B | 50 μL |
| (11) | Streptavidin APC diluted solution | 50 μL |
| (12) | PBS-B | 50 μL |
| (13) | Streptavidin APC diluted solution | 50 μL |

[Measurement and Analysis]

The amount of each of APC, FITC, and PE fluorescent dyes bound to the cell surface via an antibody specifically bound to a surface antigen was determined on FACS Canto™ (BD Co.) for cells of tube numbers (1) to (13) comparing with negative controls. Herein, Tube (2) was the negative control for tubes (6), (7) and (9); tube (3) was the negative control for tubes (10) and (12), tube (4) was the negative control for tubes (11) and (13), and tube (5) was the negative the control for tube (8). Tube (1) contained non-stained cells.

As a result, in tubes (6), (8), and (10) to (13), the amount of fluorescent dye bound to the cell surface was greater than that of the negative control, and in tubes (7) and (9), the amount of fluorescent dye bound to the cell surface was similar to that of the negative control. These results indicate that the dental pulp-derived cells are positive for CD29, CD44, CD73, DC90, CD105 and CD166, and are negative for CD34 and CD45, as with human mesenchymal stem cells.

[Measurement of Chondrogenic Differentiation Ability]

Chondrogenic differentiation ability were examined referring to the method described in Kiani C. et al., Cell Res. 12 19-32 (2002), and Aung A. et al., Arthritis Rheum. 63 148-58 (2011).

Fibronectin was added at a density of 1 µg/cm$^2$ to polyethylene terephthalate porous membrane having a pore size of 0.4 µm (track etched membrane) provided on the bottom face of 12-well insert (BD Falcon Cell Culture Insert, BD Biosciences), and then porous membrane was left undisturbed at 37° C. at least for 30 minutes to coat the membrane with fibronectin. The 12-well insert thus prepared was placed in 12-well companion plate.

The cells (1×10$^6$ cells/mL) frozen stored in liquid nitrogen were thawed, and after addition of 10 ml of DMEM (10% FBS) medium and gentle mixing, the cells were precipitated by centrifugation (1500 rpm, 5 min). The supernatant was discarded, and the cells were suspended in 10 ml of DMEM (10% FBS) medium added, and again precipitated by centrifugation (1500 rpm, 5 min). The cells then were suspended in DMEM (10% FBS) medium and seeded at a density of 5000 to 10000 cells/cm$^2$ in culture flasks, and the cells were cultured in DMEM (10% FBS) medium until the cell confluence reached 90 to 100%. The cells were washed with PBS, and added with 0.25% trypsin-EDTA, and then were left undisturbed for 5 to 10 minutes at 37° C. to be detached. DMEM (10% FBS) medium was added to suspend the cells, and the number of viable cells was counted. Dental pulp-derived cells were suspended at a concentration of 3×10$^3$ cells/mL in NH ChondroDiff Medium (Miltenyi Biotec, hereafter referred to as "NH medium"), which is a chondrogenic differentiation-inducing medium. One mL of the suspended cells was seeded in each well of the 12-well insert as prepared above and cultured for differentiation for four weeks while exchanging the medium every 3 to 4 days. This group of cells was designated chondrogenic differentiation induction group. The dental pulp-derived cells cultured with DMEM medium in the same manner was designated control group.

After incubation, total RNA was extracted from the cells of each group using RNeasy Plus Mini Kit (QIAGEN) and total RNA extract solution was prepared. The concentration of the total RNA contained in the total RNA extracted solution was then measured on a multi-mode plate reader (Molecular Devices Co.). After measurement of RNA concentration, a PCR reaction solution was prepared using TaqMan™ RNA-to-CT™ 1-Step Kit (Life Technologies), and real-time RT-PCR was performed using 25 ng of total RNA of each group under the PCR reaction condition of [(48° C./15 min)×1 cycle, (95° C./10 min)×1 cycle, and (95° C./15 sec and 62° C./1 min)×35 cycles] to amplify aggrecan gene and β-actin gene. As primers for this PCR, aggrecan probe (Assay ID/Hs00202971_m1, (Applied Biosystems, Co.) and β-actin probe (Assay ID/Hs99999903_m1, Applied Biosystems, Co.) were used, respectively.

As a result, Ct value (Threshold cycle) of aggrecan was found to be 33.8 for the control group and 28.2 for the chondrogenic differentiation induction group, respectively, revealing that the Ct value of aggrecan was lower for the chondrogenic differentiation induction group than that of the control group. This result indicates that expression levels of aggrecan, the main molecule constituting the extracellular matrix in cartilage, increased in the chondrogenic differentiation induction group, and that the dental pulp-derived cells possess the ability to differentiate into chondrocytes.

[Measurement of Osteoblast Differentiation Ability]

Osteoblast differentiation ability was examined by the following method referring to the description in Pittenger M F., et al., Science. 284, 143-7 (1999), and Colter D C., et al., Proc Natl Acad Sci USA. 98, 7841-5 (2001).

Dental pulp-derived cells, which were prepared by the same method employed as was described above in the measurement of chondrogenic differentiation ability, were seeded at a density of 5000 to 10000 cells/cm$^2$ in DMEM (10% FBS) medium in a 48-well culture plate, and cultured overnight. The cells were divided into two groups. In one of the groups, the medium was replaced with a osteoblast differentiation induction medium, which was a basal medium for osteoblast differentiation (Lonza Co.) supplemented with additional factors set (Lonza Co.) containing dexamethasone, L-glutamine, ascorbate, penicillin/streptomycin, MCGS, and β-glycerophosphate, and the cells were cultured for three weeks while exchanging the medium every 3 to 4 days to induce differentiation. This group of cells was designated as osteoblast differentiation induction group. In the other group, the medium was replaced with fresh DMEM (10% FBS) medium, and the cells were cultured for three weeks while exchanging medium every 3 to 4 days. This group of cells was designated control group. After the culture, the cells were washed once with PBS, and 0.2 mL of PBS and 0.2 mL of 2 M hydrochloric acid were added to each well, and then the cells were left undisturbed for 1 hour at 37° C. so that the calcium accumulated in the cells was released from the cells. The concentration of released calcium was determined using Calcium E-Test Wako (Wako Pure Chemical Industries). As a result, the concentration of released calcium was found to be 1.53 mg/dL in the control group, whereas the osteoblast differentiation induction group exhibited a high value of 24.88 mg/dL.

This result demonstrates that the dental pulp-derived cells differentiate into osteoblasts by incubation in an osteoblast differentiation induction medium and accumulate calcium in the cells, which shows that the dental pulp-derived cells have an ability to differentiate into osteoblasts.

[Measurement of Adipogenic Differentiation Ability]

Adipogenic differentiation ability was examined referring to the description in Gimble J M., et al., J Cell Biochem. 58. 393-402 (1995).

Dental pulp-derived cells, which were prepared by the same method as was employed in the measurement of chondrogenic differentiation ability, were seeded at a density of 5000 to 10000 cells/cm$^2$ in 24-well culture plate in DMEM (10% FBS) medium, and cultured overnight to allow them to adhere to the plate. The cells were divided into two groups. In one of the groups, the medium was replaced with an adipogenic differentiation induction medium, which was a basal medium for adipocyte differentiation (Lonza Co.) supplemented with indomethacin (final concentration, 60 µM), IBMX (final concentration, 0.5 mM), and hydrocortisone (final concentration, 0.5 µM), and the cells were cultured for 5 weeks while exchanging the medium every 3 to 4 days to induce differentiation. This group was designated adipogenic differentiation induction group. In the other group, the medium was replaced with fresh DMEM (10% FBS) medium and cultured for five weeks while replacing the medium every 3 to 4 days. This group was designated control group.

It has been known that cells that have differentiated into adipocytes form fat globules and accumulate neutral fat in the fat globules. Thus, after the culture, the cells of both groups were stained with Oil Red O (lipid assay kit, PRIMARY CELL Co.), and observed for neutral fat in the cells of both groups. Staining of neutral fat, however, was not observed in either group. Further, after the staining, Oil Red O dye was extracted using an extraction solution (lipid assay kit, PRIMARY CELL Co.), and the absorbance of the extracts was compared between the groups at 540 nm. However no significant difference was observed between the groups.

Then, the changes of expression levels of lipoprotein lipase, one of the adipocyte differentiation markers, was examined. A total RNA extraction solution was prepared by extracting total RNA from the cells of each group using RNeasy Plus Mini Kit (QIAGEN) and the concentration of RNA contained in the total RNA extraction solution was measured on a multi-mode plate reader (Molecular Devices Co.). After the measurement of RNA concentration, a PCR reaction solution was prepared using TaqMan™ RNA-to-CT™ 1-Step Kit (Life Technologies), and real-time RT-PCR was performed using 25 ng of the total RNA of each group under a PCR reaction condition [(48° C./15 min)×1 cycle), 95° C./10 min×1 cycle), and (95° C./15 sec, 60° C./1 min)×40 cycles)] to amplify the lipoprotein lipase gene and the β-actin gene. As the primers for PCR, a lipoprotein lipase probe (Assay ID: Hs00173425_m1, Applied Biosystems Co.) and a β-actin probe (Assay ID/Hs99999903_m1, Applied Biosystems Co.) were used, respectively.

As a result, as Ct values of lipoprotein lipase (Threshold cycle) were 39.3 for the control group, and for the adipogenic differentiation induction group the value was 36.0, respectively, revealing that the Ct value of LPL in the adipogenic differentiation induction group was slightly lower than that of the control group. These results, although not confirming fat globules accumulating neutral fat in the cells, demonstrate the increase in the expression levels of Lipo Protein Lipase, one of the adipocyte differentiation markers, and thus indicating the adipogenic differentiation ability, though weak.

[Measurement of Ability to Inhibit T Cell Proliferation]

After thawing human peripheral blood mononuclear cells (Lonza Co.) in a thermostatic bath at 37° C., the cells were suspended in 10 mL DMEM medium, precipitated by centrifugation (1500 rpm, 5 min), and the supernatant was removed. The cells were suspended in DMEM (10% FBS) medium added, and after the number of viable cells was counted using trypan blue staining, the cells were suspended at a concentration of $6 \times 10^6$ cells/mL. The suspension thus obtained was referred to as PBMC suspension. 5 mg of PHA-P (SIGMA Co.) was dissolved in 5 ml of DMEM (10% FBS) medium, and the resulting solution was filtrated through a 0.22 μm filter for sterilization, and then diluted with DMEM (10% FBS) culture medium 25-fold. This solution was designated PHA-P-containing medium. [Methyl-$^3$H]thymidine (Moravek Co.) was diluted 20-fold with DMEM (10% FBS) medium, and was designated Thymidine Solution.

100 μL of DMEM (10% FBS) medium was added to each of 6 wells of 96-well plate. This group was designated no-cell-addition group. Dental pulp-derived cells prepared by the same method as used in the measurement of chondrogenic differentiation ability as described above, were suspended in DMEM (10% FBS) medium at a concentration of $1 \times 10^5$ cells/mL, $2 \times 10^5$ cells/mL, or $4 \times 10^5$ cells/mL, and each of the cell suspension was added, in 100 μL aliquot, to 6 wells of 96-well plate, which were designated $1 \times 10^4$ cell group, $2 \times 10^4$ cell group, and $4 \times 10^4$ cell groups, respectively. The plate was left undisturbed for 3 to 4 hours at 37° C. under 5% $CO_2$ to let the cells attach to the bottom face of each well, and then, 50 μL of PBMC suspension was added to each well. And then 50 μL of PHA-P-containing medium was added to 3 out of 6 wells of each group, and 50 μL of DMEM (10% FBS) medium, instead of PHA-P-containing medium, was added to the remaining 3 wells. After the solution was gently mixed using a plate mixer, the cells were cultured for 3 days at 37° C. under 5% $CO_2$.

After the incubation, 20 μL of Thymidine Solution was added to every well and mixed gently using a plate mixer, and culture was continued at 37° C. under 5% $CO_2$ for further 4 hours. The cells then were collected on a filter mat using a cell harvester (Molecular Devices Co.) and dried on the filter mat. The part of the dried filter mat on which the cells were collected was cut out and placed in Glass vial, and was added with 0.8 mL of a liquid scintillation cocktail (UltimaGold MV, Perkin Elmer Co.), and then mixed on a vortex mixer. The amount of $^3$H-thymidine incorporated into the cells was determined by measuring the amount of radiation emitted from the glass vial on a liquid scintillation system (LS6500, Beckmann Co.).

For each group, the mean value of measurements for triplicate wells added with 504 of PHA-P-containing medium (mean value A) and the mean value of measurements for triplicate wells added with 50 μL of DMEM (10% FBS) medium instead of PHA-P-containing medium (mean value B) were calculated, and the amount of incorporated $^3$H-thymidine in each group was calculated by the following equation: (mean value A−mean value B). The amount of $^3$H thymidine uptake of $1 \times 10^4$ cells, $2 \times 10^4$ cells, or $4 \times 10^4$ cells was calculated as their ratio to that with the no-cell-addition group, where the amount of $^3$H thymidine uptake with the no-cell-addition group was defined as being 100% (% control).

Figure 3:
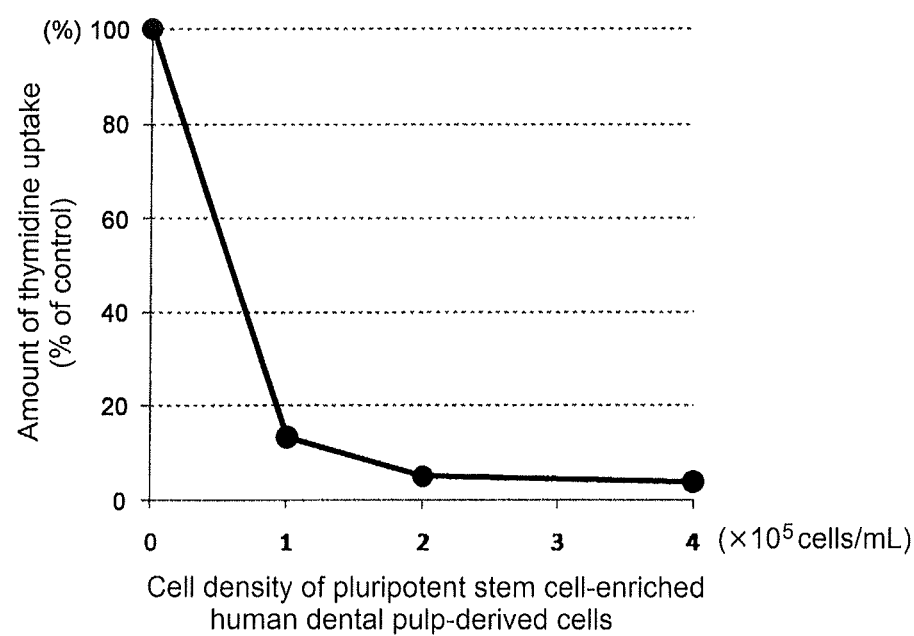
FIG. 3 A figure showing the ability of dental pulp-derived pluripotent stem cells to suppress T cell proliferation. Vertical axis: amount of thymidine uptake (percent of control), the horizontal axis: cell density of pluripotent stem cell-enriched human dental pulp-derived cells.

As a result, it was observed that the amount of $^3$H-thymidine uptake decreased in a dose-dependent manner by addition of the dental pulp-derived cells (FIG. 3). For example, with a group of $4 \times 10^4$ cells, the amount of $^3$H thymidine uptake was only about 3% of that of the no-cell-addition group. $^3$H thymidine is taken up by the cells at the time of cell division, i.e. during cell growth. Therefore, this result indicates that proliferation of peripheral blood mononuclear cells is inhibited when they are co-cultured with dental pulp-derived cells. As peripheral blood mononuclear cells are made up of immune cells such as T cells, this result indicates that the dental pulp-derived cells inhibit proliferation of immune cells, such as T cells, and thus exhibit an immunosuppressive effect. Namely, this result indicates that the dental pulp-derived cells can be used as T cell proliferation inhibitor or immunosuppressive agent, therefore as a therapeutic agent for autoimmune diseases, graft-versus-host disease.

SUMMARY

From the above results, it was confirmed that dental pulp-derived cells obtained by expansion culture as described above are pluripotent stem cells that have a brisk proliferation ability and have the ability to differentiate into two types of cells, namely, osteoblasts and chondrocytes. Furthermore, it was found that the pluripotent stem cells hardly show the ability to differentiate into adipocytes while having the ability to suppress T cell proliferation.

INDUSTRIAL APPLICABILITY

The present invention is useful for providing pluripotent stem cells derived from the dental pulp having an ability to differentiate into chondrocytes and osteoblasts and also an ability to inhibit T cell proliferation.

EXPLANATION OF SIGNS 1. 12-well insert or 6-well insert
2. 12-well companion plate or 6-well companion plate
3. Porous membrane coated with fibronectin
4. Dental pulp-derived cells
5. Feeder cells
6. Bottom well

The invention claimed is:

1. A method for production of multipotent stem cell-enriched human dental pulp-derived cells comprising the steps of,
   (a) culturing dental pulp-derived cells contained in a dental pulp suspension in a feeder cells-culture vessel containing feeder cells whose proliferative ability is suppressed, on a membrane coated with fibronectin or collagen and having micropores that can block passage of the feeder cells and supported in the feeder cells-culture vessel in a manner to prevent the lower side face thereof from contacting with the feeder cells, thereby preventing direct contact of the dental pulp-derived cells with the feeder cells,
   wherein the multipotent stem cells possess the ability to differentiate into chondrocytes and osteoblasts, and are positive for the surface antigen markers CD29, CD44, CD73, CD90, CD105, and CD166, and negative for CD34 and CD45,
   wherein the mean diameter of the micropores is 0.2 to 1.2 µm, and
   wherein the culture is conducted by using Dulbecco's modified Eagle medium containing 20% of fetal bovine serum and 3 to 5 mM of L-alanyl-L-glutamine and whose glucose concentration is 5 to 7 mM, and
   (b) recovering the cells that have proliferated on the membrane.

2. The method for production according to claim 1 further comprising:
   (c) culturing the recovered cells in a feeder cells-culture vessel containing feeder cells whose proliferative ability is suppressed, avoiding direct contact with the feeder cells, and on a membrane having micropores that can block passage of the feeder cells and supported in the feeder cells-culture vessel in order not to contact on the lower side face thereof with the feeder cells, and
   (d) recovering the cells that have proliferated on the membrane in (c).

3. The method for production according to claim 1, wherein the membrane is coated with fibronectin.

4. The method for production according to claim 1, wherein the feeder cells are mammalian cells whose proliferative ability is suppressed by mitomycin C.

5. The method for production according to claim 4, wherein the mammalian cells are NIH3T3 cells.

6. The method for production according to claim 1, wherein the culture is conducted by using Dulbecco's modified Eagle medium that contains 4 mM L-alanyl-L-glutamine and whose glucose concentration is 5.5 to 5.7 mM.

7. The method for production according to claim 1, further comprising: adding the recovered cells to a culture vessel at a density of 1000 to 20000 cells/cm$^2$; and culturing them until 70 to 100% of the bottom face of the culture vessel is occupied by the cells.

8. The method for production according to claim 1, further comprising: adding the recovered cells to a culture vessel at a density of 5000 to 10000 cells/cm$^2$; and culturing them until 90 to 100% of the bottom face of the culture vessel is occupied by the cells.

9. The method for production according to claim 1, wherein the mean diameter of the micropores is 0.4 µm.

* * * * *